United States Patent

Wurster

[11] Patent Number: 5,545,148
[45] Date of Patent: Aug. 13, 1996

[54] ENDOSCOPIC SEWING INSTRUMENT

[76] Inventor: Helmut Wurster, Mozartstrasse 20, 75038 Oberderdingen, Germany

[21] Appl. No.: 139,809

[22] Filed: Oct. 22, 1993

[30] Foreign Application Priority Data

Oct. 24, 1992 [DE] Germany ............................ 43 04 353.4

[51] Int. Cl.$^6$ ............................ A61M 5/315; A61B 17/12
[52] U.S. Cl. ............................ 604/223; 606/147; 606/205
[58] Field of Search ............................ 604/222, 223, 604/144, 148, 146; 606/147, 228, 205–207

[56] References Cited

U.S. PATENT DOCUMENTS 4,580,567  4/1986  Schweitzer et al. ............................ 606/147
4,597,390  7/1986  Mulhollan et al. ............................ 606/148

FOREIGN PATENT DOCUMENTS

0482881A1  4/1992  European Pat. Off. .
4114204    4/1991  Germany ............................ 606/148

Primary Examiner—Michael H. Thaler
Assistant Examiner—Nancy Mulcare
Attorney, Agent, or Firm—Evenson McKeown Edwards & Lenahan, PLLC

[57] ABSTRACT

Endoscopic sewing instrument with a helical-needle which has one or more windings and is Positioned between at least two rolls which drive the needle and the thread in a rotary manner.

35 Claims, 6 Drawing Sheets

ENDOSCOPIC SEWING INSTRUMENT

BACKGROUND AND SUMMARY OF THE INVENTION

The invention relates to an endoscopic sewing instrument.

In conventional endoscopic sewing instruments, such as that shown in European Patent Document EP-A1 0 482 881, a curved needle is passed through tissue and turned in the direction of its bow to make a stitch. The needle is removed from the tissue using a forceps and the needle is taken out of the sewing instrument after use.

A problem with conventional sewing instruments is that the forceps are used after each stitch to remove the needle from the tissue. To make a plurality of stitches therefore requires multiple operations for each stitch, that of moving the needle through the tissue and then grasping the needle with forceps to remove the needle from the tissue. These multiple manipulations for each stitch can lead to fatigue on the part of the surgeon and extend the length of the surgery.

There is therefore a need for an endoscopic sewing instrument that allows several stitches to be performed serially, without requiring the additional steps of grasping the needle with forceps after each stitch.

This and other needs are fulfilled by the present invention which provides an endoscopic sewing instrument comprising a plurality of rolls with at least one of the rolls being drivable, and a helical :needle connectable to a thread and having at least one winding. The needle is positionable between at least two of the rolls so as to be driven by rotation of the rolls.

Other objects, advantages and novel features of the present invention will become apparent from the following detailed description of the invention when considered in conjunction with the accompanying drawings.

DETAILED DESCRIPTION OF THE DRAWINGS

Figure 1:
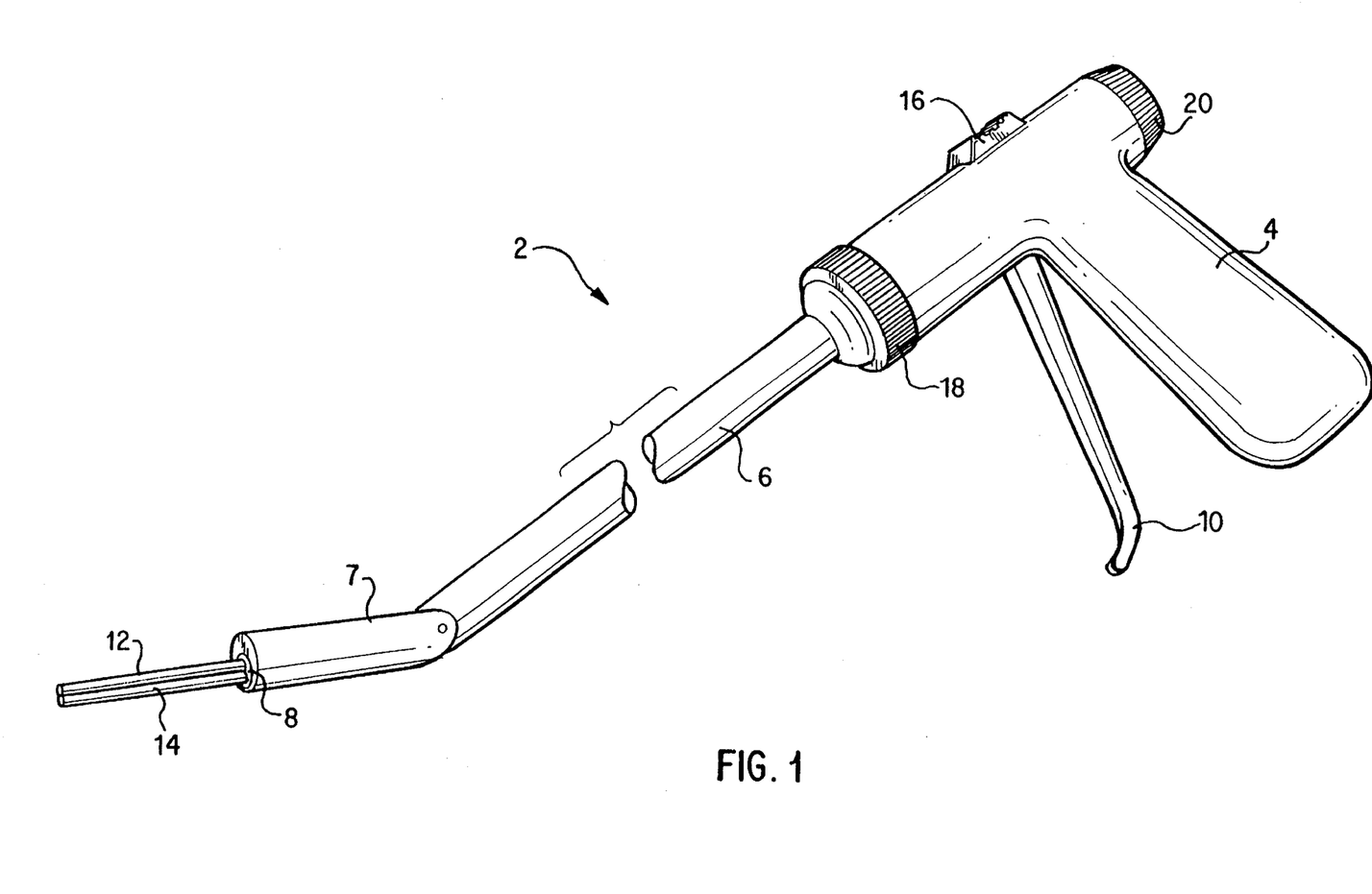
FIG. 1 shows a sewing instrument constructed in accordance with an embodiment of the present invention.

FIG. 1 shows a sewing instrument 2, comprising a handle 4, a shaft 6, a tiltable distal instrument head 7 and a rollhead 8. At the handle 4, levers 10 are provided for rotating rolls 12, 14. A pusher 16 controls opening and closing of the rolls 12, 14. A knob 18 is provided to control tilting of the distal instrument head 7. A further knob 20 is provided to control rotating of the rollhead 8.

Figure 2A:
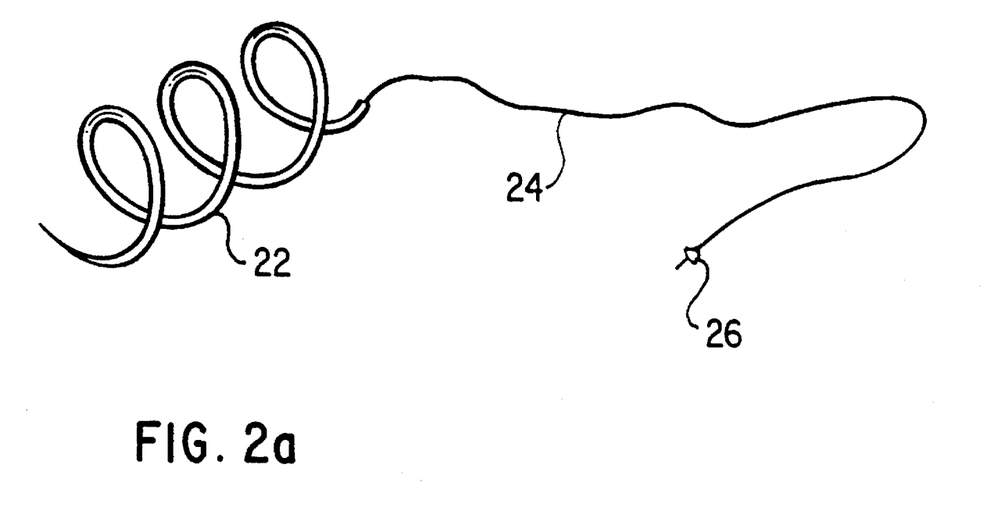
FIG. 2a shows a needle constructed in accordance with an embodiment of the present invention with an atraumatically attached thread.

FIG. 2a illustrates an embodiment of a needle 22 which is a helical coil having multiple windings. At the needle 22 a thread 24 is attached which has at its end a knot 26 or a knot clip 26.

Figure 2B:
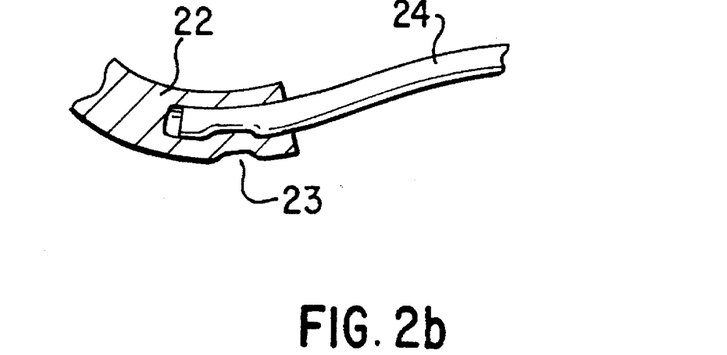
FIG. 2b illustrates an exemplary atraumatic needle-thread connection.

FIG. 2b shows an exemplary atraumatic connection between needle 22 and thread 24. The thread 24 is squeezed at a crimping part 23 of the needle 22. In a well known manner, the thread 24 could also be glued within the needle 22.

Figure 3A:
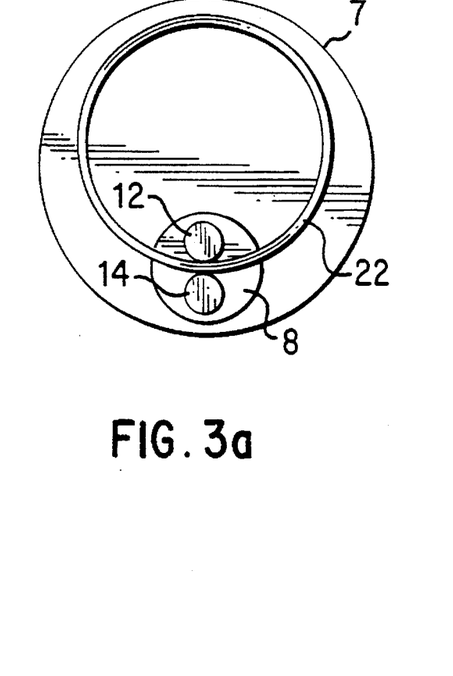
FIG. 3a shows an end view of a distal end of the sewing instrument with a needle in place and with rolls in position for introduction.
Figure 3B:
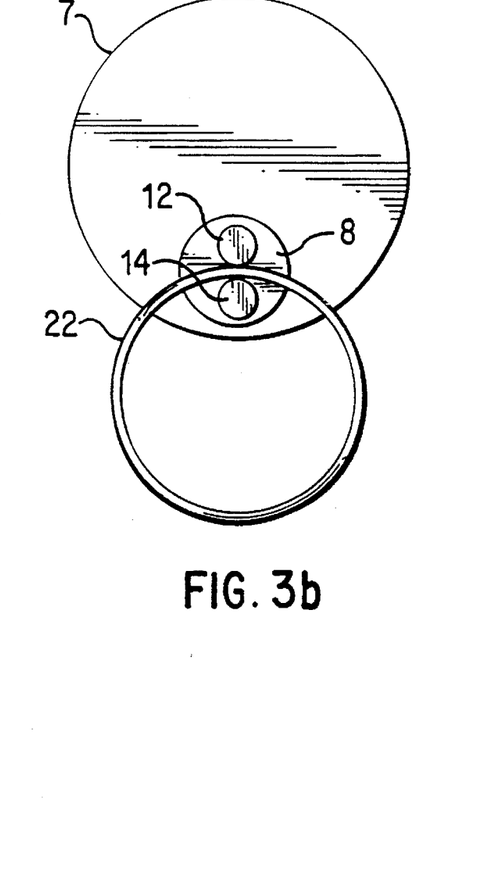
FIG. 3b is a view similar to FIG. 3a, but with the needle in place and the rolls in sewing position.
Figure 5:
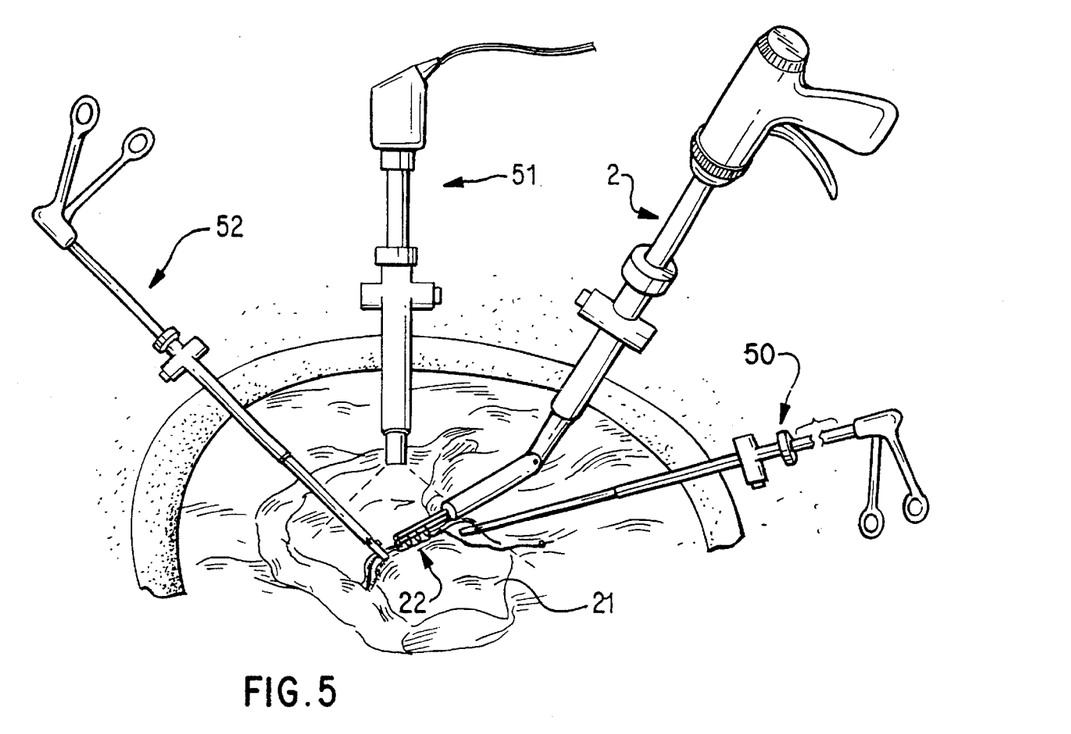
FIG. 5 illustrates endoscopic use of the sewing instrument of the present invention.
Figure 6:
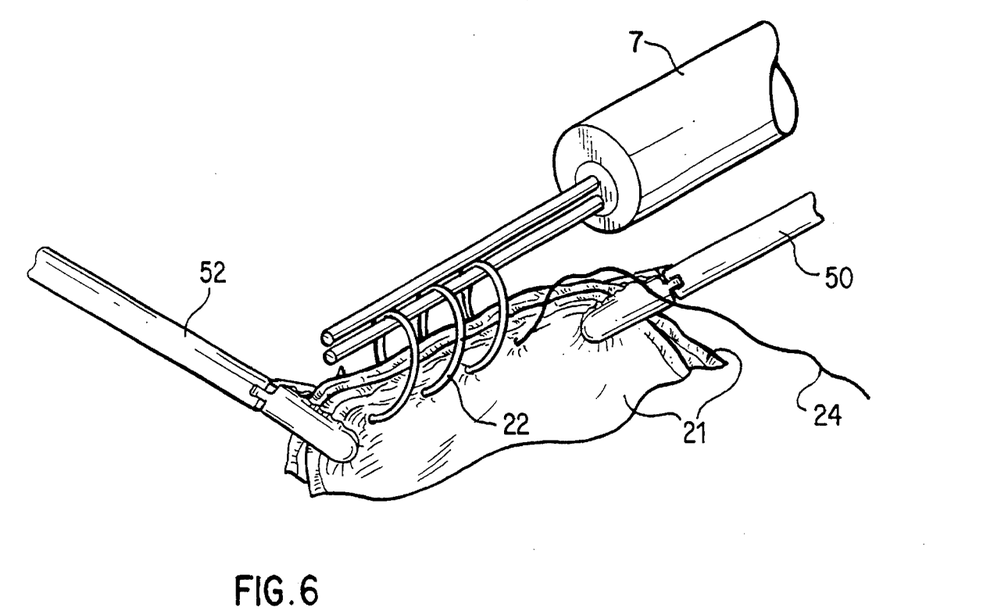
FIG. 6 is a detailed view of a part of tissue sutured with the sewing instrument.

To operate the sewing instrument, the helical needle 22 with the firmly attached thread 24 is pressed between the two rotating rolls 12, 14. The rollhead 8 is then rotated by the driven rolls 12, 14 as shown in FIGS. 3a and 3b, and thereby rotates the needle 22. As the needle 22 is rotated, its tip pierces the tissues 21 being sewed (FIG. 5 and 6). With further movement the needle 22 screws itself into the tissue 21 being sewed and connects the tissue. By proper guidance of the distal instrument head 7, the point where the tip of the needle 22 pierces the tissue 21 can be selected. The suture can be finished after the stitching, by sliding out the tip of the needle 22 from the tissue 21.

The tissues 21 to be sewed can be held together using forceps 50 and 52 and placing the tip of the needle 22 at the desired point for the first stitch as well as for the following stitches. Multiple stitches can also be made without correction if the tissue edges being sewed and the axis of the needle 22 (rolls) are correctly positioned relative to each other and are approximately parallel.

The thread 24 is also driven by the two rolls 12 and 14, which are coated with a soft plastic 13, 18, such as silicon, to provide the necessary friction between needle 22, thread 24 and the rolls 12, 14 for the rotation. The thread 24 is looped by this driving through the tissues 21. When the needle 22 has pierced the tissue layers with the desired number of stitches, the tip of the needle 22 is directed out of the tissue and the needle 22 screws itself out, so that only thread 24 remains within the tissue. The thread 24 is pulled tight using a forceps and the end is fastened using a clip or manual knot.

Figure 3C:
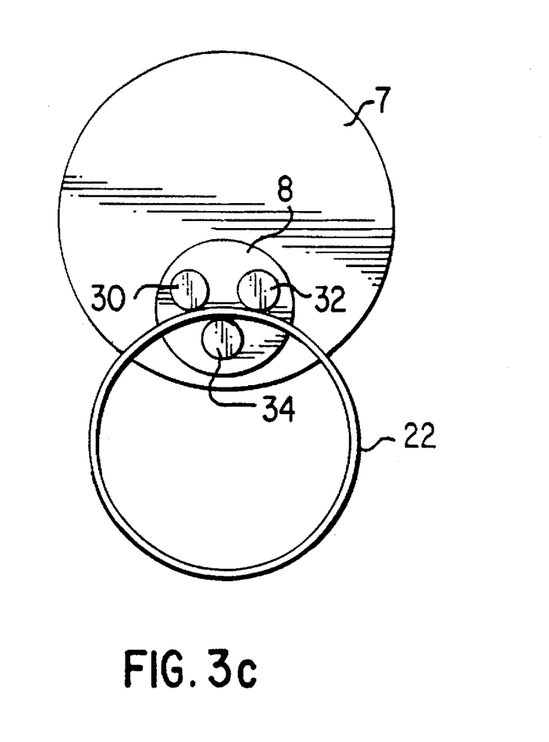
FIG. 3c illustrates another embodiment of the rollhead with three rolls and a needle in place.

As FIGS. 3a–3c show, the needle 22 is driven between the rolls 12, 14 or the three rolls 30, 32 and 34 (in an alternate embodiment), where the rolls are mounted on rollhead 8. The rollhead 8 can be turned by 180° so that the needle 22 is within the lumen of the instrument when the instrument is introduced through a trocar sleeve.

Figure 4:
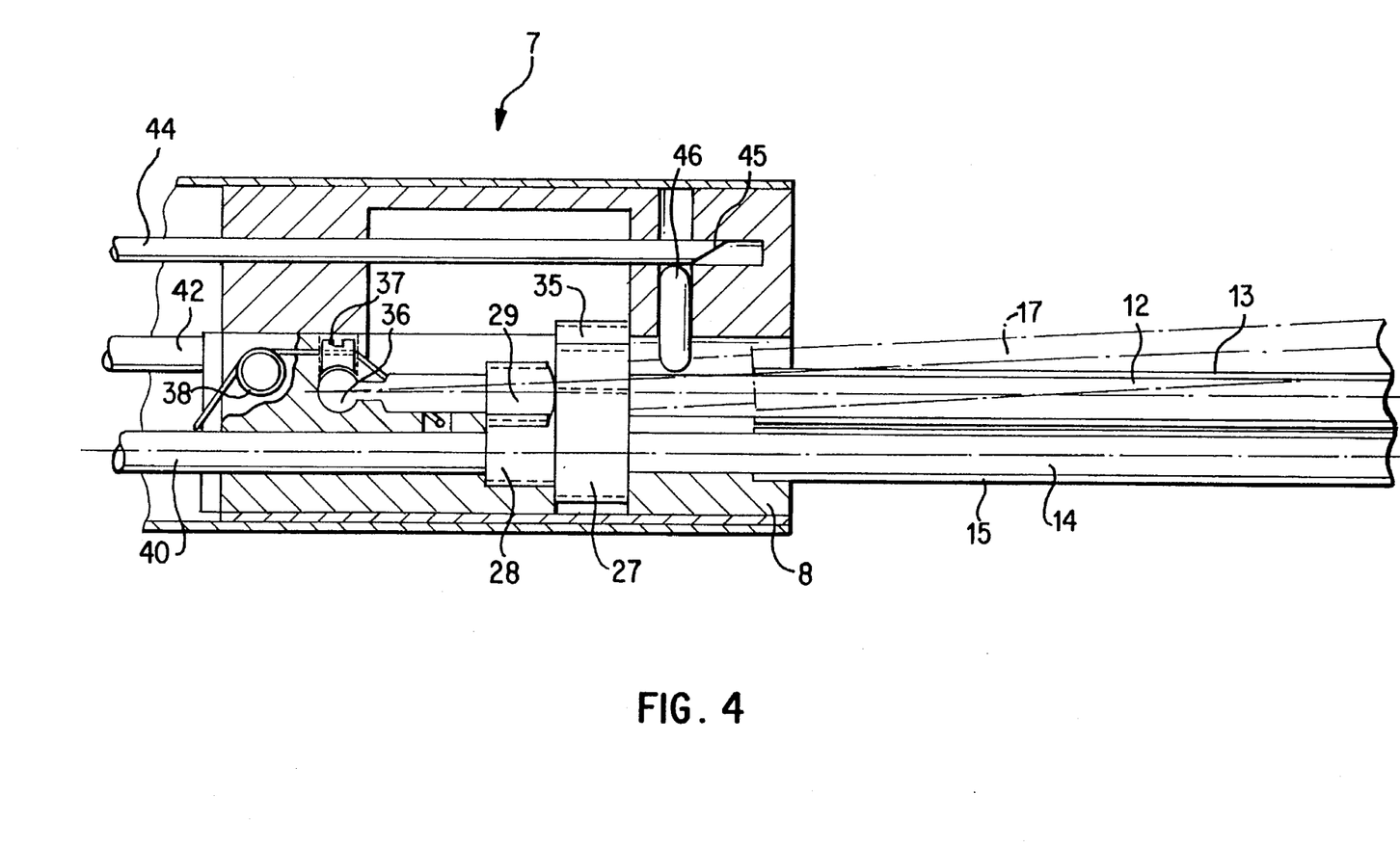
FIG. 4 is a cross-sectional view of a distal end and rollhead.

For removal of the needle 22, the rolls 12 and 14 are opened like a scissors (FIG. 4) by pusher 16. The open position is shown in FIG. 4 at 17 with the dotted line. The distal instrument head 7 of the unit is tiltable by knob 18 through a conventional tilt mechanism which operates as a fine ratchet positioning or locking device to fix the head 7 in each position and to bring the roll axis into the sewing direction, This makes the endoscopic sewing easier. The opening of roll 12 is accomplished by spring 38. The roll 12 is carried at its proximal end in a ball shaped disc 36 and fixed by a screw 37 so that it performs a rotating motion, A wedge 45 which is operated by rod 44 coupled to the pusher 16 presses pin 46 and roll 12 downwards against roll 14. The rolls 12 and 14 are respectively coupled to engageable wheels 28 and 29.

The rotating of the rollhead 8 is performed by toothed wheel 27 which is directly coupled to the rollhead 8 and a driving wheel 35 that is connected to a rod 42. The rollhead 8 can be rotated by 180° as mentioned before, for introducing the instrument together with the needle 22. The rod 44 is connected via a flexible cable to pusher 16 and rod 42 is connected with knob 20 by which the rollhead 8 could be turned.

Figure 7:
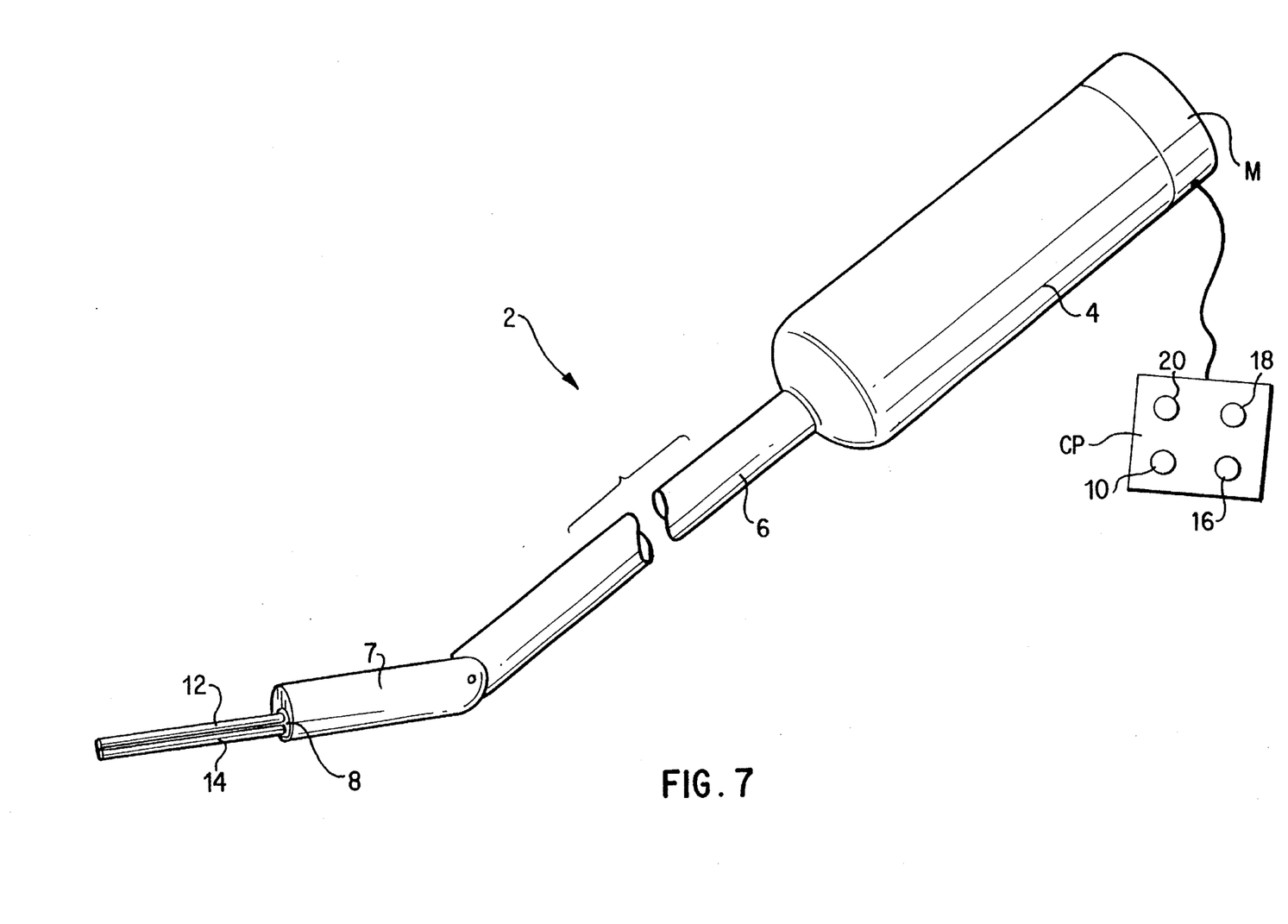
FIG. 7 illustrates another embodiment of the present invention.

The rotation of the rolls 12, 14 is accomplished by rod 40 which is directly coupled to roll 14. The rotation could also be made by an electric motor M (as seen in the embodiment of FIG. 7) or by the hand lever 10 where the hand lever 10 is operated over a ratchet so that one movement of the lever cause one rotation or portion thereof of the needle, One rotation of the needle 22 corresponds to one stitch. The operator can rotate the needle 22 controlled by himself and position it to the desired pier(ting point. In the embodiment of FIG. 7, each of the different controlled movements are motorized and under the control of the surgeon through control panel CP.

The manual method has the advantage that during the suture the physician can control the instrument himself and is not left only to an automatic mechanical process, e.g., using motor driven needles which may sometimes be difficult to control. The endoscopic suture operation is shown in FIG. 5. For the operation,, besides the sewing instrument 2, an endoscopic optic with video camera 51 as well as grasping forceps 50 and 52 are used. The tissue to be sutured is held by grasping forceps 50 and 52 as illustrated in FIG. 6. The sewing instrument with its needle 22 and thread 24 is introduced through the trocar sleeve. After introduction, the rollhead 8 is turned via knob 20 by 180° so that the needle 22 is positioned in its working position. The axis of the rolls 12, 14 is brought parallel to the suture direction by rotating knob 18, adjusting the tilting angle of the sewing instrument 2. The needle 22 is then brought to the tissue 21 to be sutured. By operating handle 10, the rolls 12, 14 are rotated to thereby rotate the needle 22. Directing the tissue with the forceps and the sewing instrument itself will influence the progress of the suture.

To adapt the suture to medical requirements it is necessary to have needles with different pitches to provide the proper distance between the stitches of multiple stitches. The pitch of the needle should be between 3 and 8 mm. The distance of the stitches can also be corrected within a certain range by manually moving the sewing instrument. The number of windings of the needle 22 should be such that the position of the needle 22 within the rolls 12, 14 is stable, requiring at least two windings within the rolls 12, 14. The needle 22 is thereby prevented from turning in the direction of the rolls 12, 14. Two windings of the needle 22 also result in a higher driving moment transmitted by friction to the needle 22.

A needle 22 having a number of windings between 1.25 and 1.5 also could be used. Such a needle 22 is only stable if the overlapping part is between the rolls 12, 14 and could be used for single stitches. For making a longer suture, a needle having 2 to 5 windings will be advantageous, whereby the number of windings should not be greater than the number of stitches being made, otherwise the needle does more stitches in the tissue than desired.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed:

1. An endoscopic sewing instrument comprising:

a plurality of rolls, with at least one of the rolls being drivable;

a helical needle connectable to a thread and having at least one winding, the needle being positionable between at least two of the rolls so as to be rotatably driven by rotation of the rolls, and a controllable motor drivingly coupled to the rolls to selectively rotate the needle in one of complete or partial rotations.

2. An endoscopic sewing instrument comprising:

a plurality of rolls, with at least one of the rolls being drivable;

a helical needle connectable to a thread and having at least one winding the needle being positionable between at least two of the rolls so as to be rotatably driven by rotation of the rolls, and a roll head eccentrically positionable with respect to an instrument axis to introduce the instrument through the trocar sleeve with the needle in place, the roll head carrying the rolls.

3. Endoscopic sewing instrument according to claim 2, further comprising a hand-operated lever coupled to the rolls and a ratchet such that a complete movement of the lever causes one of a full turn of the needle or a partial turn of the needle.

4. Endoscopic sewing instrument according to claim 2, further comprising a pusher coupled to at least one of the rolls to open the rolls to allow placement or removal of the needle between the rolls.

5. Endoscopic sewing instrument according to claim 2, wherein the rollhead is rotatable by 180° via a knob to, locate the needle in a working position.

6. Endoscopic sewing instrument according to claim 2, wherein the helical needle has one to five windings.

7. Endoscopic sewing instrument according to claim 2, wherein the needle has a tip with cutting edges.

8. Endoscopic sewing instrument comprising:

a plurality of rolls, with at least one of the rolls being drivable;

a helical needle connectable to a thread and having at least one winding, the needle being positionable between at least two of the rolls so as to be rotatably driven by rotation of the rolls to perform suturing by driving rotation of the at least one drivable roll, and a distal instrument head coupled to a knob, the knob controlling tilting of the head, the head being lockable in each position.

9. Endoscopic sewing instrument according to claim 8, wherein the rolls have a coating to thereby increase friction to the needle.

10. Endoscopic sewing instrument comprising:

a plurality of rolls, with at least one of the rolls being drivable; and a helical needle connectable to a thread and having at least one winding, the needle being positionable between at least two of the rolls so as to be rotatably driven by rotation of the rolls to perform suturing by driving rotation of the at least one drivable roll, and wherein the rolls have a coating of silicon rubber to thereby increase friction to the needle.

11. Endoscopic sewing instrument according to claim 10, wherein the rolls are made of hard material are and knurled at their surface.

12. Endoscopic sewing instrument comprising:

a plurality of rolls, with at least one of the rolls being drivable; and a helical needle connectable to a thread and having at least one winding, the needle being positionable between at least two of the rolls so as to be rotatably driven by rotation of the rolls to perform suturing by driving rotation of the at least one drivable roll, wherein thread is atraumtically attachable to the needle.

13. A sewing instrument for suturing tissue by rotating a helical needle to pass through tissue and pull a thread attached to the needle, said helical needle including at least one helical winding and being operable to form one thread stitch in the tissue for each helical winding, said sewing instrument including:

a plurality of rolls selectively engageable with a helical needle to grip the helical needle between said rolls, and roll driving means for rotatably driving at least one of the rolls to thereby rotatably drive the helical needle with the helical needle penetrating tissue and pulling a thread to form at least one threaded stitch in the tissue and subsequently moving out of the tissue to accommodate separation of the needle and thread after formation of the at least one threaded stitch.

14. A sewing instrument according to claim 13, wherein said roll driving means includes a manually operable pivoting lever and ratchet mechanism which is configured to drive the at least one drivable roller to thereby drive the helical needle only in a forward stitching direction with each successive pivoting movement of the lever, said ratchet mechanism preventing movement of the drivable roller and gripped needle in a direction opposite the stitching direction.

15. A sewing instrument according to claim 14, wherein said roll driving means includes means for driving the at least one of the rolls in one rotation direction by an amount sufficient to perform multiple stitches with a corresponding multiple number of helical windings in a needle being driven.

16. A sewing instrument according to claim 13, wherein said roll driving means includes an electric motor for driving the at least one drivable :roller to thereby drive the helical needle in a forward stitching direction.

17. A sewing instrument according to claim 16, wherein said roll driving means includes means for driving the at least one of the rolls in one rotation direction by an amount sufficient to perform multiple stitches with a corresponding multiple number of helical windings in a needle being driven.

18. A sewing instrument according to claim 13, wherein said sewing instrument is an endoscopic instrument which is introducible along with a helical needle and attached thread to a tissue to be sutured through a trocar sleeve.

19. A sewing instrument according to claim 13, wherein said roll driving means includes means for driving the at least one of the rolls-in one rotation direction by an amount sufficient to perform multiple stitches with a corresponding multiple number of helical windings in a needle being driven.

20. A sewing instrument according to claim 13, comprising:

a gripping handle, a shaft connected to and protruding from the handle, and a roll head supported for pivotal movement at an end of the shaft remote from the handle, wherein said plurality of rolls are supported in the roll head, and wherein said driving means includes manually engageable drive control means on the handle.

21. A sewing instrument according to claim 20, comprising:

a manually engageable pivot control member at said handle for accommodating control of pivotal movement of the roll head with respect to the shaft, said pivot control member being separate from and spaced from the drive control means.

22. A sewing instrument according to claim 21, wherein said sewing instrument is an endoscopic instrument which is introducible along with a helical needle and attached thread to a tissue to be sutured through a trocar sleeve.

23. A sewing instrument according to claim 22, comprising manually operable roll head moving means at the handle for moving the roll head between a trocar insertion accommodating position and a needle working position.

24. A sewing instrument according to claim 23, wherein said roll head moving means includes means for rotating the needle 180° from its trocar insertion accommodating position to its needle working position.

25. A sewing instrument according to claim 13, wherein said rolls are configured to drivingly engage a thread end attached to a helical needle to thereby force the helical needle out of the tissue in the same direction as the stitching direction.

26. A sewing instrument for suturing tissue by rotating a helical needle to pass through tissue and pull a thread attached to the needle, said helical needle including at least one helical winding and being operable to form one thread stitch in the tissue for each helical winding, said sewing instrument including:

a gripping handle, a shaft connected to and protruding from the gripping handle, a roll head supported at an end of the shaft remote from the gripping handle, a plurality of rolls in said roll head extending adjacent one another and having respective gripping surfaces for gripping a helical needle therebetween, at least one of the rolls being rotatably drivable so that a helical needle gripped between said rolls can be rotatably driven to perform suturing operations with the helical needle first penetrating the tissue, followed by movement of the needle and attached thread through the tissue to form at least one threaded stitch and subsequent continued rotation of the needle to a position outside of the tissue to accommodate separation of the needle and thread after formation of the at least one threaded stitch.

27. A sewing instrument according to claim 26, wherein said roll head is supported for pivotal movement with respect to the shaft so as to accommodate variable positioning of the roll head and gripped needle with respect to the handle for a tissue stitching operation.

28. A sewing instrument according to claim 27, comprising a manually operable pivoting lever and ratchet mechanism supported at the handle and operable to rotatably drive the at least one drivable roller to thereby drive the helical needle in a forward stitching direction with each successive pivoting movement of the lever.

29. A sewing instrument according to claim 26, comprising a manually operable pivoting lever and ratchet mechanism supported at the handle and operable to rotatably drive the at least one drivable roller to thereby drive the helical needle in a forward stitching direction with each successive pivoting movement of the lever.

30. A sewing instrument according to claim 26, comprising an electric motor for driving the at least one drivable roller to thereby drive the helical needle in a forward stitching direction.

31. A sewing instrument according to claim 27, wherein said sewing instrument is an endoscopic instrument which is introducible along with a helical needle and attached thread to a tissue to be sutured through a trocar sleeve.

32. A sewing instrument according to claim 31, comprising manually operable roll head moving means at the handle for moving the roll head between a trocar insertion accommodating position and a needle working position.

33. A sewing instrument according to claim 32, wherein said roll head moving means includes means for rotating the needle 180° from its trocar insertion accommodating position to its needle working position.

34. A sewing instrument according to claim 26, wherein said rolls are configured to drivingly engage a thread end attached to a helical needle to thereby force the helical needle out of the tissue in the same direction as the stitching direction.

35. A sewing instrument according to claim 27, comprising an electric motor for driving the at least one drivable roller to thereby drive the helical needle in a forward stitching direction.

* * * * *